United States Patent
Matsumoto (10) Patent No.: US 9,746,485 B2
(45) Date of Patent: Aug. 29, 2017

(54) AUTOMATIC BLOOD COAGULATION ANALYSIS DEVICE

(71) Applicant: SHIMADZU CORPORATION, Kyoto-shi, Kyoto (JP)

(72) Inventor: Junichi Matsumoto, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 14/823,155

(22) Filed: Aug. 11, 2015

(65) Prior Publication Data

US 2017/0045539 A1   Feb. 16, 2017

(51) Int. Cl.
*G01N 35/02* (2006.01)
*G01N 33/49* (2006.01)
*G01N 21/01* (2006.01)
*G01N 21/17* (2006.01)
*G01N 35/00* (2006.01)
*G01N 21/00* (2006.01)

(52) U.S. Cl.
CPC ....... *G01N 35/00693* (2013.01); *G01N 21/00* (2013.01); *G01N 33/4905* (2013.01); *G01N 35/025* (2013.01)

(58) Field of Classification Search
CPC ......... G01N 35/025; G01N 2035/0439; G01N 2035/0453; G01N 33/4905; G01N 2035/0455
See application file for complete search history.

(56) References Cited

U.S. PATENT DOCUMENTS

| 4,777,141 A | * | 10/1988 | Calzi | G01N 21/82 422/72 |
| 2007/0002309 A1 | * | 1/2007 | Yamamoto | G01N 21/253 356/39 |
| 2008/0318323 A1 | * | 12/2008 | Shintani | B01L 3/5082 436/47 |

FOREIGN PATENT DOCUMENTS

| JP | S57-161537 A | 10/1982 |
| JP | H07-026766 U | 5/1995 |
| JP | 3324560 B2 | 9/2002 |

OTHER PUBLICATIONS

Japanese Office Action corresponding to Japanese Patent Application No. 2013-025971, dated May 24, 2016.

* cited by examiner

*Primary Examiner* — Paul Hyun
(74) *Attorney, Agent, or Firm* — Sughrue Mion, PLLC (57) ABSTRACT

An automatic blood coagulation analysis device including a computation processing unit which executes computation processing according to a pre-installed program, and a storage unit which stores data acquired from outside and data obtained through computation processing by the computation processing unit. The computation processing unit comprises an Fbg computation module, a correction coefficient computation module, a reference value setting module and a difference module. The storage unit comprises a standard sample measured value holding unit, base value holding unit, standard sample difference value holding unit, reference value holding unit, correction coefficient holding unit, specimen measured value holding unit and specimen difference value holding unit.

13 Claims, 6 Drawing Sheets

AUTOMATIC BLOOD COAGULATION ANALYSIS DEVICE

TECHNICAL FIELD

The present invention relates to an automatic blood coagulation analysis device which automatically analyzes blood coagulation reaction in the field of clinical laboratory testing.

BACKGROUND ART

Automatic blood coagulation analysis devices which automatically measure blood coagulation reaction sample a specimen and reagent by means of a probe from containers holding the specimen and reagent, dispense these into empty cuvettes, place those cuvettes into predetermined measurement ports and execute optical measurement (see Patent Literature 1). One of the measurement parameters of such automatic blood coagulation analysis devices is the measurement of fibrinogen concentration (hereinafter, Fbg concentration) in the specimen.

Measurement of Fbg concentration is performed by adding a thromboplastin reagent (containing tissue thromboplastin and calcium; hereinafter, PT reagent) to the specimen, irradiating the reaction solution with light, and measuring scattered light. When PT reagent is added to the specimen, as the final reaction, the fibrinogen within the specimen changes to fibrin. Fibrinogen is soluble in water, and hardly scatters any light when irradiated with light, while fibrin is insoluble in water and produces scattering when irradiated with light. The intensity of scattered light from the reaction solution to which PT reagent has been added is proportional to the amount of fibrin in the reaction solution, and the amount of fibrin in the reaction solution depends on the amount of fibrinogen in the specimen, so the Fbg concentration in the specimen can be determined by measuring final scattered light intensity from the reaction solution to which PT reagent has been added.

PRIOR ART LITERATURES

Patent Literature (Patent literature 1) Japanese Patent No. 3324560

SUMMARY OF THE INVENTION

Problem to be Solved by the Invention

By providing scattered light measurement units which irradiate cuvettes with light and measure the resulting scattered light at multiple locations, it becomes possible to simultaneously execute Fbg concentration measurement of multiple specimens, making it possible to improve the analysis efficiency in cases where there is a large number of specimens. However, since there are individual differences among the scattered light measurement units in terms of the intensity of light irradiated onto the cuvettes, the distance from the light source to the cuvettes, the distance from the cuvettes to the photo-sensor, etc., when the same cuvette is measured with different scattered light measurement units, the same scattered light intensity will not be obtained. Thus, when multiple specimens are measured with multiple scattered light measurement units, there is the problem that the measurement results are affected by individual differences among the individual scattered light measurement units and the measurement precision becomes worse as compared to the case where multiple specimens are sequentially placed into and measured with a single scattered light measurement unit.

It is thus an object of the present invention to make it possible to measure multiple specimens with high precision using multiple scattered light measurement units.

Means for Solving the Problem

The automatic blood coagulation analysis device of the present invention comprises: a plurality of stray light measurement units which comprise a plurality of measurement ports removably holding cuvettes containing a specimen and reagent, and which irradiate the cuvettes held in each measurement port with light and measure the resulting scattered light intensity with a light detector; a correction coefficient holding unit which holds a correction coefficient for each of the scattered light measurement units, which coefficient reduces the variability of measured values due to individual differences among the scattered light measurement units by correcting the measured values obtained in each of the scattered light measurement units; and an Fbg computation module which determines fibrinogen concentration using the corrected measured values obtained by correcting the measured values obtained in each of the scattered light measurement units with the corresponding correction coefficient.

Effect of the Invention

The automatic blood coagulation analysis device of the present invention comprises a correction coefficient holding unit which holds a correction coefficient for each scattered light measurement unit, which coefficient reduces the variability of measured values due to individual differences among the scattered light measurement units by correcting the measured values obtained in each scattered light measurement unit, and an Fbg computation module which determines fibrinogen concentration using the corrected measured values obtained by correcting the measured values obtained in each of the scattered light measurement units with the corresponding correction coefficient, thus making it possible to reduce variability of measured values due to individual differences among scattered light measurement units and to determine the Fbg concentration of specimens with high efficiency and high precision using multiple scattered light measurement units.

DETAILED DESCRIPTION OF THE EXEMPLARY EMBODIMENTS

It is preferable to additionally provide the automatic blood coagulation analysis device of the present invention with a standard sample measured value holding unit which holds, as standard sample measured values, the measured values of each scattered light measurement unit obtained by measuring the scattered light intensity in a state where cuvettes containing standard sample are held in the measurement ports; a reference value setting module which sets a reference value to be used for computation of a correction coefficient, on the basis of the standard sample measured value for each scattered light measurement unit; and a correction coefficient computation module which computes correction coefficients by dividing the standard sample measured value for each scattered light measurement unit by the reference value. In this way, the device can be made to compute a correction coefficient for each scattered light measurement unit.

In the above case, the reference value setting module may set the minimum value, maximum value or mean value of the standard sample measured values as the reference value.

The present invention can additionally be provided with a base value holding unit wherein detection signals of the light detector for each scattered light measurement unit, obtained by measuring the scattered light intensity in a state where no cuvettes are held in the measurement ports, are held as base values for the respective scattered light measurement units; and a standard sample difference value holding unit wherein a value obtained by subtracting the base value from the standard sample measured value for each scattered light measurement unit is held as the standard sample difference value for each scattered light measurement unit. In this case, it is preferable if the reference value setting module sets the reference value based on the standard sample difference value for each scattered light measurement unit held in the standard sample difference value holding unit, and the correction coefficient computation module computes the correction coefficients by dividing the standard sample difference value for each scattered light measurement unit held in the standard sample difference value holding unit by the reference value set in the reference value setting module. By using detection signals of the light detector of each scattered light measurement unit obtained by measuring scattered light intensity in a state where no cuvettes are held in the measurement ports as base values, and subtracting the base value from the specimen measured value, it is possible to accurately measure the pure scattered light from the specimen and increase the precision of measurement of scattered light intensity.

In the above case as well, the reference value setting module may set the minimum value, maximum value or mean value of the standard sample measured values as the reference value.

Latex reagent or fibrin precipitation reaction liquid can be mentioned as an example of the standard solution. Fibrin precipitation reaction liquid is a reaction liquid obtained by mixing PT reagent with control blood plasma and leaving to rest.

Figure 1:
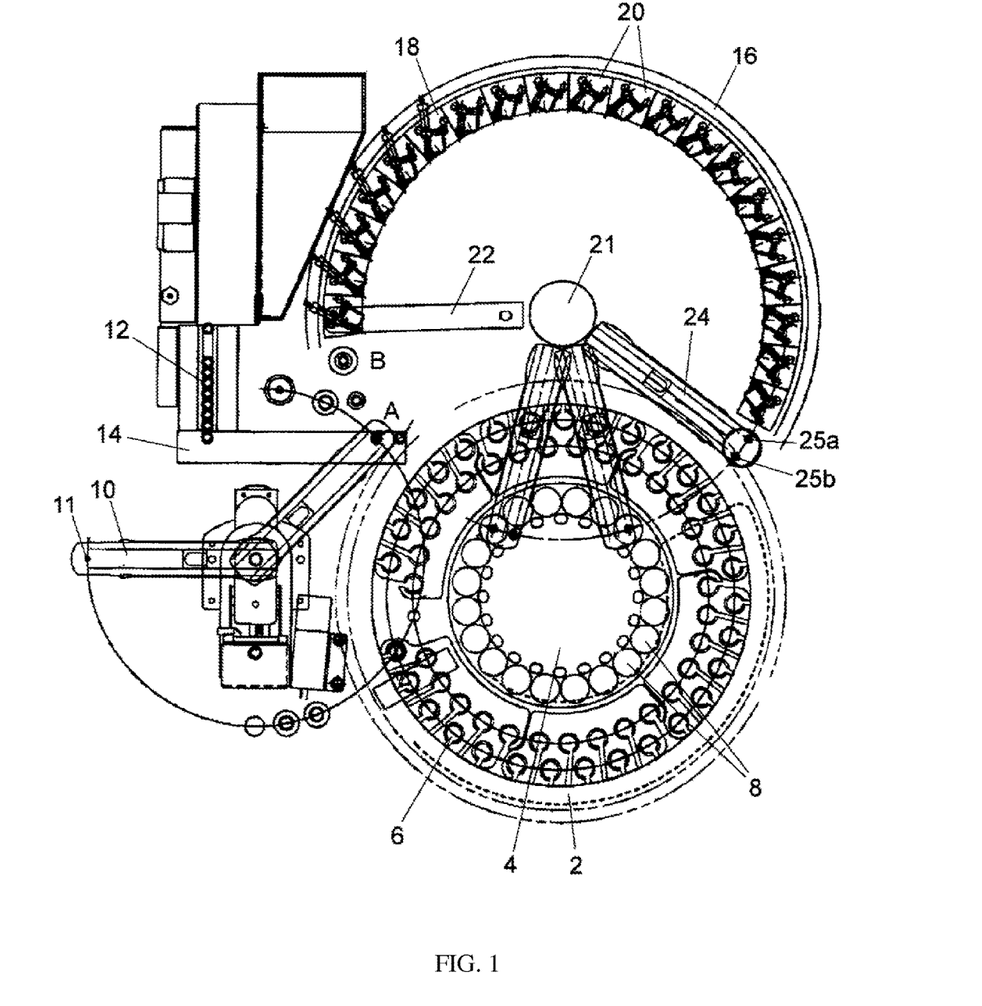
FIG. 1 is a plan view illustrating an embodiment example of an automatic blood coagulation analysis device.

An embodiment example of an automatic blood coagulation analysis device will be described using FIG. 1.

There is provided a specimen table 2 on the circumference of which are arranged multiple specimen holding units 6 which hold specimens, and a reagent table 4 on the circumference of which are arranged multiple reagent holding units 8 which hold reagent. The reagent table 4 is a table with a round planar shape, the center of which is rotationally driven by a shaft, and which allows arbitrary reagent holding units 8 to be arranged at predetermined reagent sampling locations. The specimen table 2 is a table which surrounds the outer circumference of the reagent table 4 and has specimen holding units 6 on a circumference concentric with the reagent table 4. The specimen table 2 is rotationally driven independently of the reagent table 4, and allows predetermined specimen holding units 6 to be arranged at predetermined specimen sampling locations.

A specimen arm 10 which samples and transports specimens from the specimen holding unit 6 is arranged to the side of the specimen table 2. The specimen arm 10 retains on its tip end part a specimen sampling probe 11 which performs suction and dispensing of specimens, rotates about a shaft at its base end part, and is able to move the specimen sampling probe 11 to a predetermined location on the circumference of its movement track.

Near the specimen arm 10, there is provided a cuvette transport mechanism 14 which transports empty cuvettes 12. A specimen dispensing location A is provided on the movement track of the specimen sampling probe 11, and the cuvette transport mechanism 14 transports cuvettes to the specimen dispensing location A. At the specimen dispensing location A, specimens are dispensed from the specimen sampling probe 11 into cuvettes 12 which have been transported to this location A.

A measurement unit 16 is provided near the specimen table 2 and reagent table 4. In the measurement unit 16, multiple transmitted light measurement units 18 and multiple scattered light measurement units 20 are arranged in a series so as to describe a common circular arc. The transmitted light measurement units 18 and scattered light measurement units 20 both comprise measurement ports in which cuvettes 12 containing specimens are placed.

Illustration of the transmitted light measurement units 18 has been omitted, but in a transmitted light measurement unit 18, light is irradiated onto a cuvette placed into a measurement port, and the resulting transmitted light intensity is measured.

Figure 2:
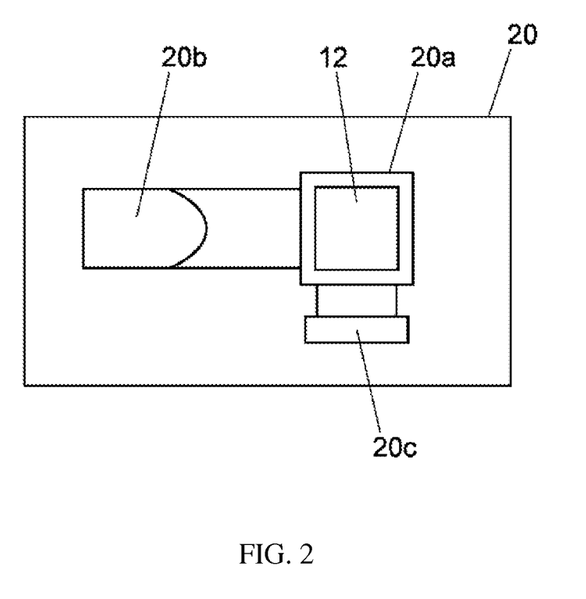
FIG. 2 is a plan view schematically illustrating a scattered light measurement unit of the same embodiment example.

In the scattered light measurement units 20, as shown in FIG. 2, light from a light source 20b is irradiated onto a cuvette 12 placed into a measurement port 20a, and scattered light from the cuvette 12 is measured with a detector 20c arranged at a position 90° to the optical axis from the light source 20b.

Returning to FIG. 1, a central shaft 21 is provided at the center of the circular arc described by the transmitted light measurement units 18 and scattered light measurement units 20. A cuvette transport arm 22 and reagent arm 24 are provided, which are rotationally driven about the axis of the central shaft 21. The cuvette transport arm 22 and reagent arm 24 are driven independently of each other.

A cuvette holding unit (illustration omitted) which holds a cuvette 12 is provided on the tip end part of the cuvette transport arm 22. The specimen dispensing location A is located over the movement track of the specimen sampling probe 11 at the tip end of the specimen arm 10 and at the same time is located over the movement track of the cuvette holding unit on the tip end part of the cuvette transport arm 22. The cuvette transport arm 22 takes hold of a cuvette 12 at the specimen dispensing location A and transports it to an arbitrary scattered light measurement unit 20 or to agitation location B.

Two reagent sampling probes 25a, 25b are provided at the tip end part of the reagent arm 24. The reagent arm 24 moves the reagent sampling probes 25a, 25b to a predetermined reagent sampling location over the reagent table 4, and arbitrary reagents are sampled by the reagent sampling probes 25a and 25b in conjunction with the rotation of the reagent table 4. The reagent arm 24 moves the reagents sampling arms 25a, 25b which have sampled a reagent to the location of a cuvette 12 placed into an arbitrary scattered light measurement unit 20 or at agitation location B, and dispenses reagent into the cuvette 12.

The data obtained by each of the measurement units 18, 20 is fed into a personal computer (PC) or specialized computer, and various types of computation processing are executed. The computer which executes the computation processing is configured so as to perform correction in order to increase the accuracy of the measurement results for measurement of fibrinogen concentration (Fbg concentration) in the specimens.

Figure 4:
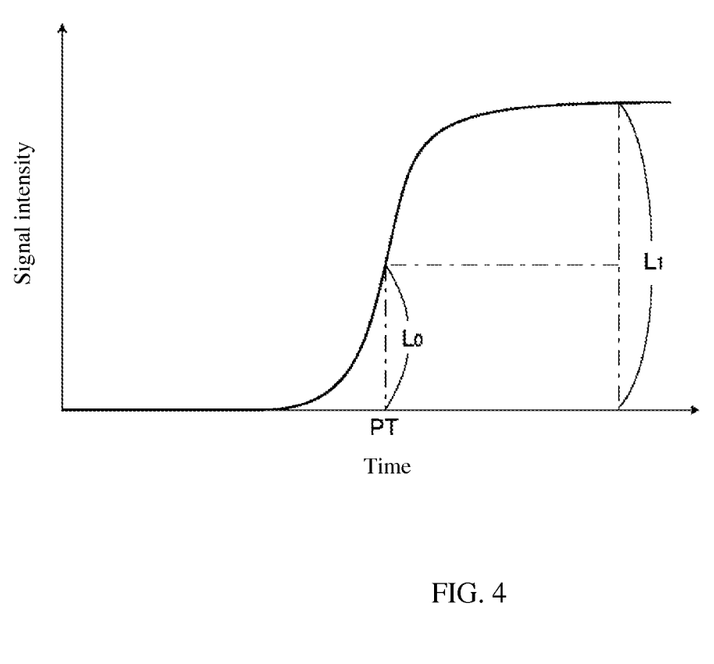
FIG. 4 is a diagram illustrating an example of the waveform of the signal obtained in a scattered light measurement unit.

Here, in the measurement of Fbg concentration, data as shown in FIG. 4 is obtained by adding PT reagent to the specimen and measuring the change over time of scattered light intensity. By means of such measurement, it is possible to measure the PT (prothrombin time), which is the time until the specimen coagulates, and the Fbg concentration. PT is defined as the time in which the signal intensity reaches an intensity L0 which is a preset proportion (for example, 40%) of the signal intensity L1 when scattered light intensity is at equilibrium. Furthermore, Fbg concentration can be determined based on the final signal intensity (scattered light intensity) L1 when scattered light intensity has reached equilibrium.

Figure 3:
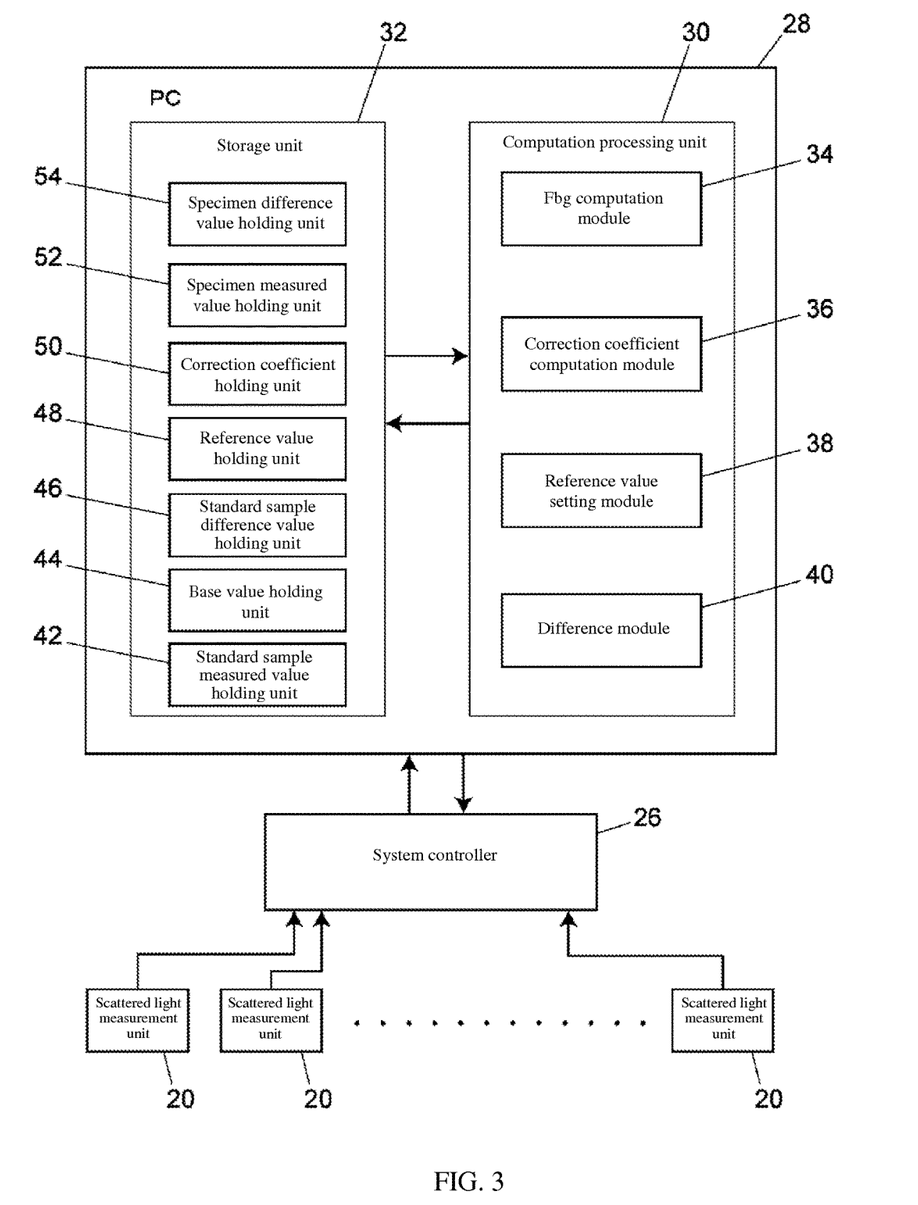
FIG. 3 is a block diagram schematically illustrating the signal system for Fbg concentration measurement of the same embodiment example.

FIG. 3 shows an example of a signal system for Fbg concentration measurement in the automatic blood coagulation analysis device of the present embodiment example. In this example, a personal computer (PC) is used as the computer which performs computation processing for Fbg concentration measurement.

PC 28 is connected to this automatic blood coagulation analysis device via a system controller 26 which controls the operation of the tables 2 and 4, the arms 10, 22 and 24, and the cuvette transport mechanism 14. The measurement data obtained in each scattered light measurement unit 20 is fed into the PC 28 via the system controller 26.

PC 28 is provided with a computation processing unit 30 which executes computation processing according to a pre-installed program, and a storage unit 32 which stores data acquired from outside and data obtained through computation processing by the computation processing unit 30. The computation processing unit 30 comprises an Fbg computation module 34, a correction coefficient computation module 36, a reference value setting module 38 and a difference module 40. The storage unit 32 comprises a standard sample measured value holding unit 42, base value holding unit 44, standard sample difference value holding unit 46, reference value holding unit 48, correction coefficient holding unit 50, specimen measured value holding unit 52 and specimen difference value holding unit 54.

Figure 5:
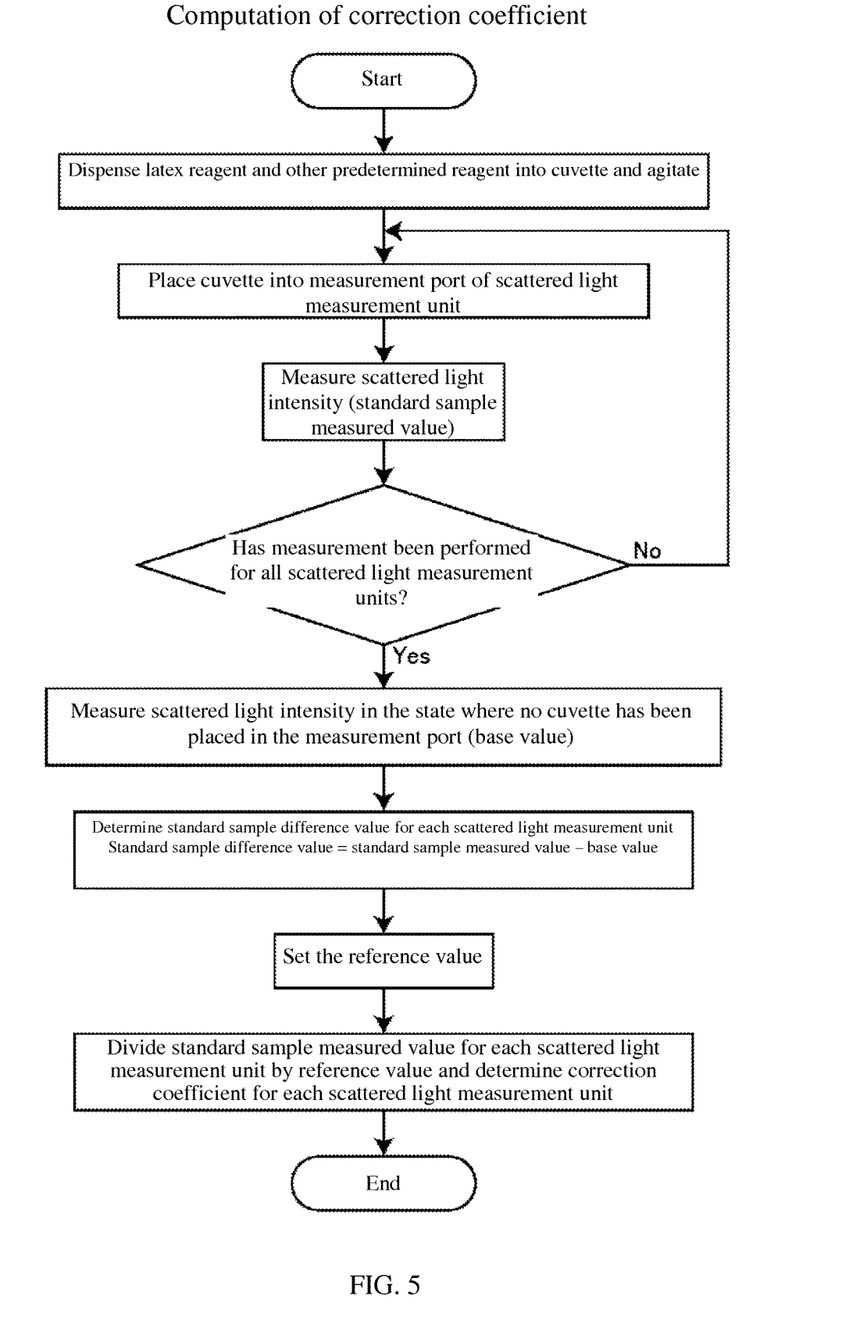
FIG. 5 is a flowchart illustrating the correction coefficient computation operation of the same embodiment example.

The correction coefficient computation operation of the same embodiment example will be described using FIG. 1, FIG. 3 and FIG. 5.

First, an empty cuvette 12 is transported by the cuvette transport arm to the reagent dispensing and agitation location B. A latex reagent (standard sample) and another predetermined reagent are sampled by the reagent arm 24, dispensed into the cuvette 12, and agitated. The cuvette 12 is held and transported by the cuvette transport arm 22 and placed into a measurement port of one of the scattered light measurement units 20, and measurement of scattered light intensity is performed. Here, the acquired data (standard sample measured value) is held in standard sample measured value holding unit 42 of storage unit 32. Once measurement of scattered light intensity is completed, the same cuvette 12 is transported by the cuvette transport arm 22 to another scattered light measurement unit 20, and measurement of scattered light intensity is performed with the other scattered light measurement unit 20. This standard sample measured value acquisition operation is executed for all the scattered light measurement units 20, and a standard sample measured value for each scattered light measurement unit 20 is retained in the standard sample measured value holding unit 42. As the standard sample, in addition to latex reagent, for example, a PT reaction liquid in which fibrin has precipitated can be used. These are both reagents which are used in blood coagulation devices. In addition to these, substances used as turbidity standard liquids, such as formazine and polystyrene, can also be employed.

After a standard sample measured value has been acquired for all the scattered light measurement units 20, the scattered light intensity in the state where no cuvette is placed in the measurement port (base value) is measured for each of the scattered light measurement units 20, and the acquired base values are retained in the base value holding unit 44 of storage unit 32. This base value acquisition operation may also be executed prior to the standard sample measured value acquisition operation. Furthermore, the base value acquisition operation and standard sample measured value acquisition operation may also be executed for each scattered light measurement unit 20 prior to measuring the scattered light from a specimen with that scattered light measurement unit 20. In this way, it is possible to eliminate the effect of variation in light source intensity.

The difference module 40 of the computation processing unit 30 obtains the difference between the standard sample measured value and the base value for each scattered light measurement unit 20, and those difference values (standard sample difference values) are retained in the standard sample difference value holding unit 46 of the storage unit 32. The reference value setting module 38 sets the minimum of the determined standard sample difference values as the reference value, and the set reference value is retained in reference value holding unit 48. It should be noted that the present invention is not limited hereto: the maximum standard sample difference value may also be set as the reference value, or the mean value of all standard sample difference values may be set as the reference value.

The correction coefficient computation module 36 computes correction coefficients by dividing the standard sample difference value of each scattered light measurement unit 20 by the reference value. The correction coefficients obtained here are retained in correction coefficient holding unit 50. An example of the data obtained through the operation described above is shown in Table 1.

TABLE 1

| | Measurement unit No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Reagent | 5670 | 5523 | 5736 | 5374 | 5670 | 5676 | 5729 | 5794 | 6106 | 6041 | 5695 | 5683 | 5583 | 5055 |
| Base | 244 | 280 | 257 | 308 | 244 | 271 | 254 | 257 | 220 | 233 | 214 | 191 | 245 | 261 |
| Difference | 5426 | 5243 | 5479 | 5426 | 5066 | 5405 | 5475 | 5537 | 5886 | 5808 | 5481 | 5492 | 5338 | 4794 |
| Correction coefficient | 1.13 | 1.09 | 1.14 | 1.13 | 1.06 | 1.13 | 1.14 | 1.15 | 1.23 | 1.21 | 1.14 | 1.15 | 1.11 | 1.00 |

In Table 1, the top row is the numbers of the measurement units (scattered light measurement units); in this embodiment example, scattered light measurement units 20 Nos. 1 through 14 are present. The second row from the top is the measured values for cuvettes containing latex reagent (standard sample measured values), the third row from the top is the base values obtained by measuring in a state where no cuvettes are installed, the fourth row from the top is the standard sample difference values (standard sample measured value–base value), and the bottommost row is correction coefficients. In this example, the standard sample difference value for scattered light measurement unit 20 No. 14 is the lowest, and using this standard sample difference value 4794 as a reference, the standard sample difference value for each scattered light measurement unit 20 is divided by the reference value 4794 to determine the correction coefficient.

Figure 6:
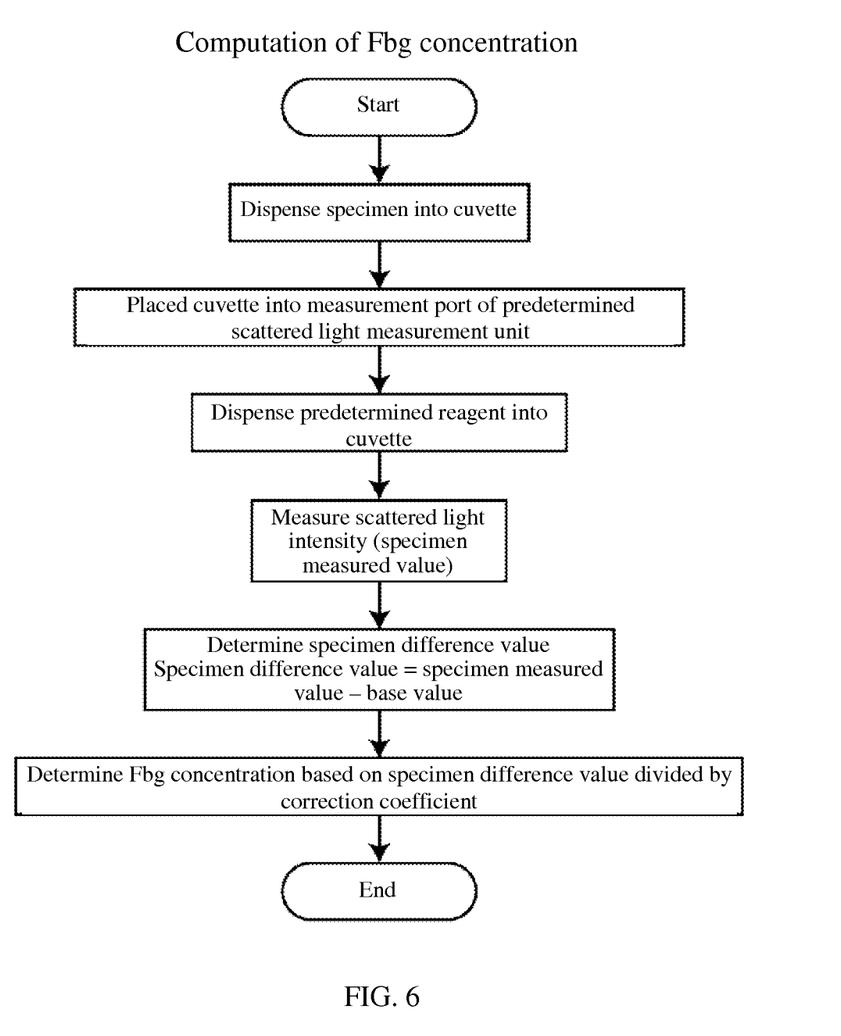
FIG. 6 is a flowchart illustrating the Fbg concentration measurement operation of the same embodiment example.

Next, the Fbg concentration measurement operation in the same embodiment example will be described using FIG. 1, FIG. 3 and FIG. 6.

An empty cuvette 12 is transported to the specimen dispensing location A. A specimen is sampled from a predetermined specimen holding unit 6 with the specimen arm 10 and is dispensed into the cuvette 12 at the specimen dispensing location A. The cuvette 12 is held and transported by the cuvette transport arm 22 and is placed into the measurement port of a predetermined scattered light measurement unit 20, PT reagent is sampled with the slide member 24 and dispensed into the cuvette 12, and measurement of scattered light intensity is performed. The measurement data (specimen measurement value) obtained here is retained in the specimen measured value holding unit 52 of storage unit 32.

The difference module 40 of the computation processing unit 30 determines the specimen difference value by subtracting the base value for the scattered light measurement unit 20 which performed the measurement from the specimen measured value obtained through said measurement. The specimen difference value is retained in the specimen difference value holding unit 54 of the storage unit 32. The Fbg computation module 34 of the computation processing unit 30 determines the specimen fibrinogen concentration based on the value (corrected measured value) obtained by dividing the specimen difference value determined here by the correction coefficient for the corresponding scattered light measurement unit 20, and outputs it to the monitor or other display device (illustration omitted) of PC 28. The base value used for determining the specimen difference value may be the one measured when computing the correction coefficient or may be newly measured immediately before or immediately after measuring stray light from the specimen.

It should be noted that in the correction coefficient computation operation and Fbg concentration measurement operation, the base value of each scattered light measurement unit need not necessarily be subtracted from the standard sample measured value and specimen measured value. For example, in cases where it can be determined based on the base value measurement results that the difference among the base values of the scattered light measurement units 20 is so small as to be negligible, the standard sample measured value can be used as-is to determine the correction coefficient, without subtracting the base value therefrom in the correction coefficient computation operation. Furthermore, in the Fbg concentration measurement operation, the specimen measured value without subtraction of the base value therefrom can be corrected using the corresponding correction coefficient, and the Fbg concentration can be determined based on that corrected value.

Table 2 shows the results of testing for the variability of measured values of scattered light intensity in each scattered light measurement unit 20 in the case where the correction coefficient of the bottommost row of Table 1 was used and in the case where it was not used.

TABLE 2

| | CV (%) | |
|---|---|---|
| | Correction coefficient not used | Correction coefficient used |
| Specimen 1 | 4.02 | 2.24 |
| Specimen 2 | 5.88 | 3.47 |

The coefficient of variation CV (%) above is determined based on CV = (standard deviation/mean) × 100

For the above test, Fbg concentration measurement was performed in all the scattered light measurement units 20 on specimen 1 and specimen 2, and the variability of the measurement results was determined in terms of coefficient of variation CV (%). The left side of Table 2 (correction coefficient not used) shows the CV determined using measurement data for scattered light intensity obtained by measuring a cuvette containing specimen 1 and scattered light intensity obtained by measuring a cuvette containing specimen 2, while the right side of Table 2 (correction coefficient used) shows the CV determined using values obtained by subtracting the base value of each scattered light measurement unit 20 from the measurement data and then dividing by the correction coefficient. As these test results demonstrate, when using values obtained by subtracting the base value from the measurement data and dividing by the correction coefficient, the variability among the scattered light measurement units 20 becomes smaller and the reproducibility of Fbg concentration measurement results among the scattered light measurement units 20 increases.

DESCRIPTION OF REFERENCES

2 Specimen table
4 Reagent table
6 Specimen holding unit

8 Reagent holding unit
10 Specimen arm
11 Specimen sampling probe
12 Cuvette
14 Cuvette transport mechanism
16 Measurement unit
18 Transmitted light measurement unit
20 Scattered light measurement unit
21 Central shaft
22 Cuvette transport arm
24 Reagent arm
25a, 25b Reagent sampling probe
26 System controller
28 Personal computer
30 Computation processing unit
32 Storage unit
34 Fbg computation module
36 Correction coefficient computation module
38 Reference value setting module
40 Difference module
42 Standard sample measured value holding unit
44 Base value holding unit
46 Standard sample difference value holding unit
48 Reference value holding unit
50 Correction coefficient holding unit
52 Specimen measured value holding unit
54 Specimen difference value holding unit

What is claimed is:

1. An automatic blood coagulation analysis device, comprising:
a plurality of scattered light measurement units each comprising a measurement port removably holding a cuvette containing a specimen and reagent, wherein said scattered light measurement units irradiate the cuvettes held in each measurement port with light and measure the resulting scattered light intensity with a light detector;
a storage holding a correction coefficient for each of said scattered light measurement units, wherein each correction coefficient reduces the variability of measured values due to individual differences among said scattered light measurement units by correcting the measured values obtained in each of said scattered light measurement units, wherein the storage further holds respective values representing the individual differences among said scattered light measurement units;
a processor; and
a computer readable medium storing a program that, when executed by the processor, causes the processor to:
set a statistic of said values representing the individual differences among said scattered light measurement units as a reference value to be used for computation of correction coefficients;
compute correction coefficients by using said values representing the individual differences among said scattered light measurement units and said reference value;
correct the measured values obtained in each of said scattered light measurement units with the corresponding correction coefficient; and
determine fibrinogen concentration using the corrected measured values.

2. The automatic blood coagulation analysis device as described in claim 1,
wherein the values representing the individual differences among said scattered light measurement units are measured values of each of said scattered light measurement units obtained by measuring the scattered light intensity in a state where cuvettes containing standard sample are held in said measurement ports; and
wherein the program, when executed by the processor, causes the processor to:
compute correction coefficients by dividing said values representing the individual differences among said scattered light measurement units by said reference value.

3. The automatic blood coagulation analysis device as described in claim 2, wherein the program, when executed by the processor, causes the processor to set the minimum value, maximum value or mean value of said values representing the individual differences among said scattered light measurement units as said reference value.

4. The automatic blood coagulation analysis device as described in claim 2, wherein said standard sample comprises a latex reagent or a fibrin precipitation reaction liquid.

5. The automatic blood coagulation analysis device as described in claim 1,
wherein the storage further holds:
as standard sample measured values, measured values of each of said scattered light measurement units obtained by measuring the scattered light intensity in a state where cuvettes containing standard sample are held in said measurement ports; and
as base values for the respective scattered light measurement units, detection signals of said light detector for each said scattered light measurement unit obtained by measuring the scattered light intensity in a state where no cuvettes are held in said measurement ports;
wherein the values representing the individual differences among said scattered light measurement units are obtained by subtracting the base value from the standard sample measured value for each said scattered light measurement units, and
wherein the program, when executed by the processor, causes the processor to:
compute said correction coefficients by dividing said values representing the individual differences among said scattered light measurement units by said reference value.

6. The automatic blood coagulation analysis device as described in claim 5, wherein the program, when executed by the processor, causes the processor to correct the measured values obtained in each of said scattered light measurement units with the corresponding correction coefficient by, for a given measured value of the measured values obtained in a given scattered light measurement unit of said scattered light measurement units, causing the processor to:
obtain a specimen difference value by subtracting the base value corresponding to the given scattered light measurement unit from the given measured value; and
obtain a corrected measured value for the given measured value by dividing the specimen difference value by the correction coefficient corresponding to the given scattered light measurement unit.

7. The automatic blood coagulation analysis device as described in claim 5, wherein the program, when executed by the processor, causes the processor to set the minimum value, maximum value or mean value of said values representing the individual differences among said scattered light measurement units as said reference value.

8. An automatic blood coagulation analysis method, comprising:

irradiating cuvettes containing a specimen and reagent with light, the cuvettes respectively held in a plurality of scattered light measurement units, each scattered light measurement unit including a measurement port that removably holds the respective cuvette;

measuring the resulting scattered light intensity with a light detector using the plurality of scattered light measurement units;

obtaining respective values representing individual differences among said scattered light measurement units;

setting by a processor a statistic of said values representing the individual differences among said scattered light measurement units as a reference value to be used for computation of the correction coefficients;

computing by the processor correction coefficients by using said values representing the individual differences among said scattered light measurement units and said reference value;

correcting by the processor the measured values obtained in each of said scattered light measurement units with a respective corresponding correction coefficient for each of said scattered light measurement units, the correction coefficients reducing the variability of measured values due to the individual differences among said scattered light measurement units by correcting the measured values obtained in each of said scattered light measurement units; and determining by the processor a fibrinogen concentration using the corrected measured values.

9. The automatic blood coagulation analysis method as described in claim 8, further comprising:

obtaining the values representing the individual differences among said scattered light measurement units by measuring the scattered light intensity of each of said scattered light measurement units in a state where cuvettes contain standard sample in said measurement ports;

computing by the processor correction coefficients by dividing said values representing the individual differences among said scattered light measurement units by said reference value.

10. The automatic blood coagulation analysis method as described in claim 9, further comprising setting a minimum value, maximum value or mean value of said values representing the individual differences among said scattered light measurement units as said reference value.

11. The automatic blood coagulation analysis method as described in claim 9, wherein said standard sample comprises a latex reagent or a fibrin precipitation reaction liquid.

12. The automatic blood coagulation analysis method as described in claim 8, further comprising:

obtaining, as standard sample measurement values, measured values for each of said scattered light measurement units by measuring the scattered light intensity in a state where cuvettes containing standard sample are held in said measurement ports;

obtaining, as base values for the respective scattered light measurement units, detection signals of said light detector for each said scattered light measurement unit by measuring the scattered light intensity in a state where no cuvettes are held in said measurement ports, wherein the values representing the individual differences among said scattered light measurement units are obtained by subtracting the base value from the standard sample measured value for each said scattered light measurement units; and computing by the processor said correction coefficients by dividing said values representing the individual differences among said scattered light measurement units by said reference value.

13. The automatic blood coagulation analysis method as described in claim 12, wherein correcting by the processor the measured values obtained in each of said scattered light measurement units with a respective corresponding correction coefficient for each of said scattered light measurement units further comprises, for a given measured value of the measured values obtained in a given scattered light measurement unit of said scattered light measurement units:

obtaining a specimen difference value by subtracting the base value corresponding to the given scattered light measurement unit from the given measured value; and obtaining a corrected measured value for the given measured value by dividing the specimen difference value by the correction coefficient corresponding to the given scattered light measurement unit.

* * * * *